US007443417B1

(12) United States Patent
Heinrich

(10) Patent No.: US 7,443,417 B1
(45) Date of Patent: Oct. 28, 2008

(54) METHOD OF PERFORMING DENTAL WORK AND APPARATUS PROVIDING VISION ENHANCEMENT DENTISTRY

(76) Inventor: Geoffrey W Heinrich, 800 Brinsmere Dr., Elm Grove, WI (US) 53122

( * ) Notice: Subject to any disclaimer, the term of this patent is extended or adjusted under 35 U.S.C. 154(b) by 1033 days.

(21) Appl. No.: 10/335,390

(22) Filed: Dec. 30, 2002

Related U.S. Application Data

(63) Continuation-in-part of application No. 09/451,354, filed on Dec. 13, 1999, now abandoned.

(51) Int. Cl.
*H04N 7/18* (2006.01)
(52) U.S. Cl. ....................................................... 348/66
(58) Field of Classification Search ................... 348/42, 348/51, 66, 49, 98, 43, 44, 77, 82, 85, 86; 433/31, 39; 362/268; 600/117, 249; *H04N 7/18*
See application file for complete search history.

(56) References Cited

U.S. PATENT DOCUMENTS

| 4,101,957 | A | * | 7/1978 | Chang | 362/268 |
| 4,260,376 | A | * | 4/1981 | Litel et al. | 433/29 |
| 4,779,965 | A | * | 10/1988 | Beecher | 359/720 |
| 4,915,626 | A | * | 4/1990 | Lemmey | 433/31 |
| 5,403,191 | A | * | 4/1995 | Tuason | 434/262 |
| 5,408,992 | A | * | 4/1995 | Hamlin et al. | 600/109 |
| 5,545,120 | A | * | 8/1996 | Chen et al. | 600/117 |
| 5,661,519 | A | * | 8/1997 | Franetzki | 348/66 |
| 5,687,259 | A | * | 11/1997 | Linford | 382/294 |
| 5,803,905 | A | * | 9/1998 | Allred et al. | 600/249 |
| 5,867,210 | A | * | 2/1999 | Rod | 348/51 |
| 6,414,708 | B1 | * | 7/2002 | Carmeli et al. | 348/42 |
| 6,417,881 | B1 | * | 7/2002 | Hara et al. | 348/66 |
| 7,171,114 | B2 | * | 1/2007 | Milton | 396/287 |
| 2002/0086262 | A1 | * | 7/2002 | Rainey | 433/29 |
| 2006/0001740 | A1 | * | 1/2006 | Fujie et al. | 348/66 |

FOREIGN PATENT DOCUMENTS

JP 07-275202 * 10/1995

OTHER PUBLICATIONS

Magazine Article From Dentistry Today, Jun. 2001, pp. 92-96. Author; Geoffrey Heinrich, Title: Video-Assisted Vision: a New . . . .

* cited by examiner

*Primary Examiner*—Tung Vo
(74) *Attorney, Agent, or Firm*—Donald J. Ersler

(57) ABSTRACT

A method of performing dental work without directly viewing an operative field utilizing an apparatus providing vision enhancement in dentistry. A dental camera apparatus enables the display of a mirror images of an operative field on a video display. A dentist can utilize the video mirror images as a frame of reference when performing dental work. The dental camera apparatus further provides video magnification of an object. The dental camera apparatus also includes adjustable lighting of the operative field. The dental camera apparatus may be recorded. The dental camera apparatus can be easily moved and rotated to any position offering extreme macro close-ups.

17 Claims, 4 Drawing Sheets

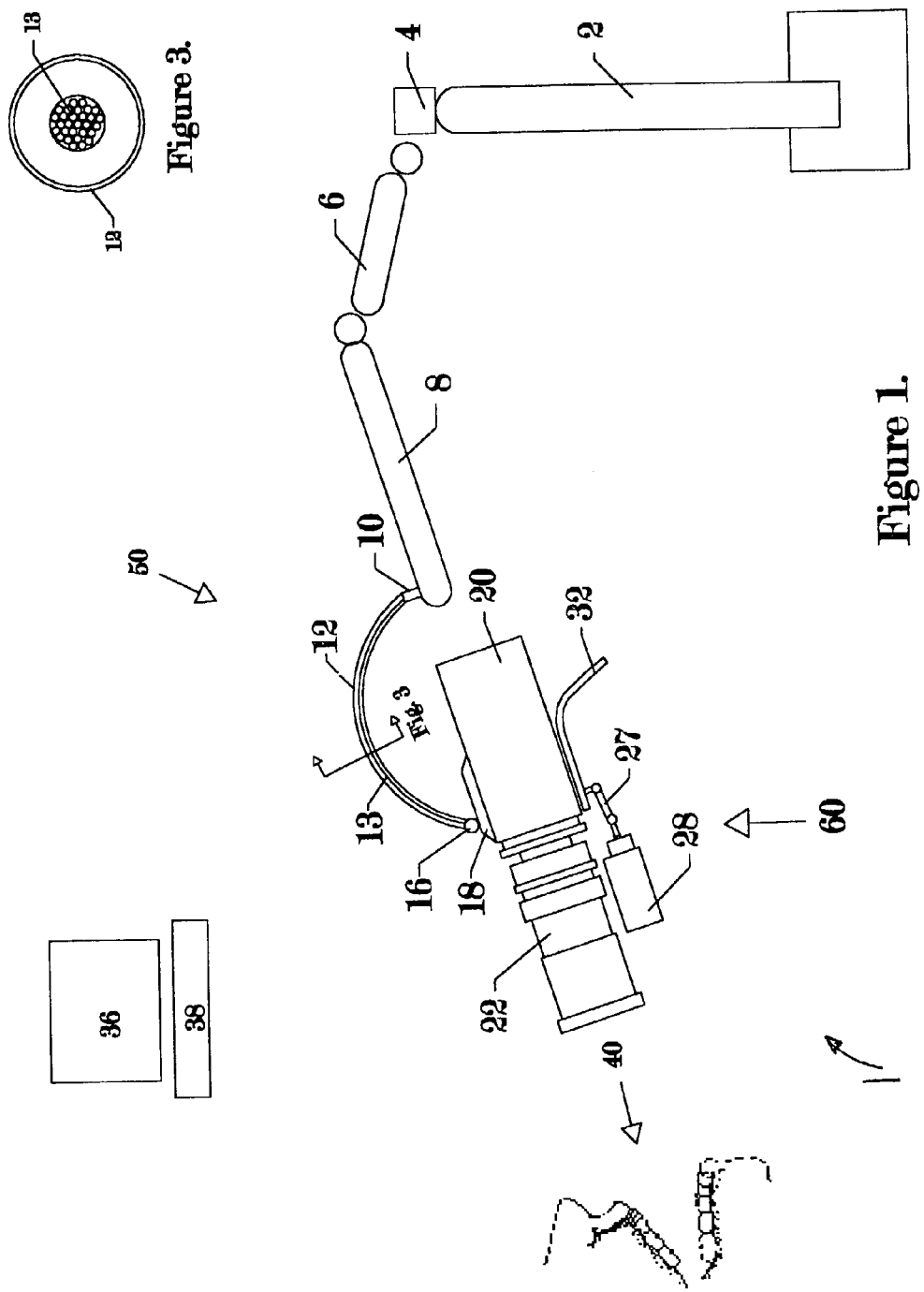

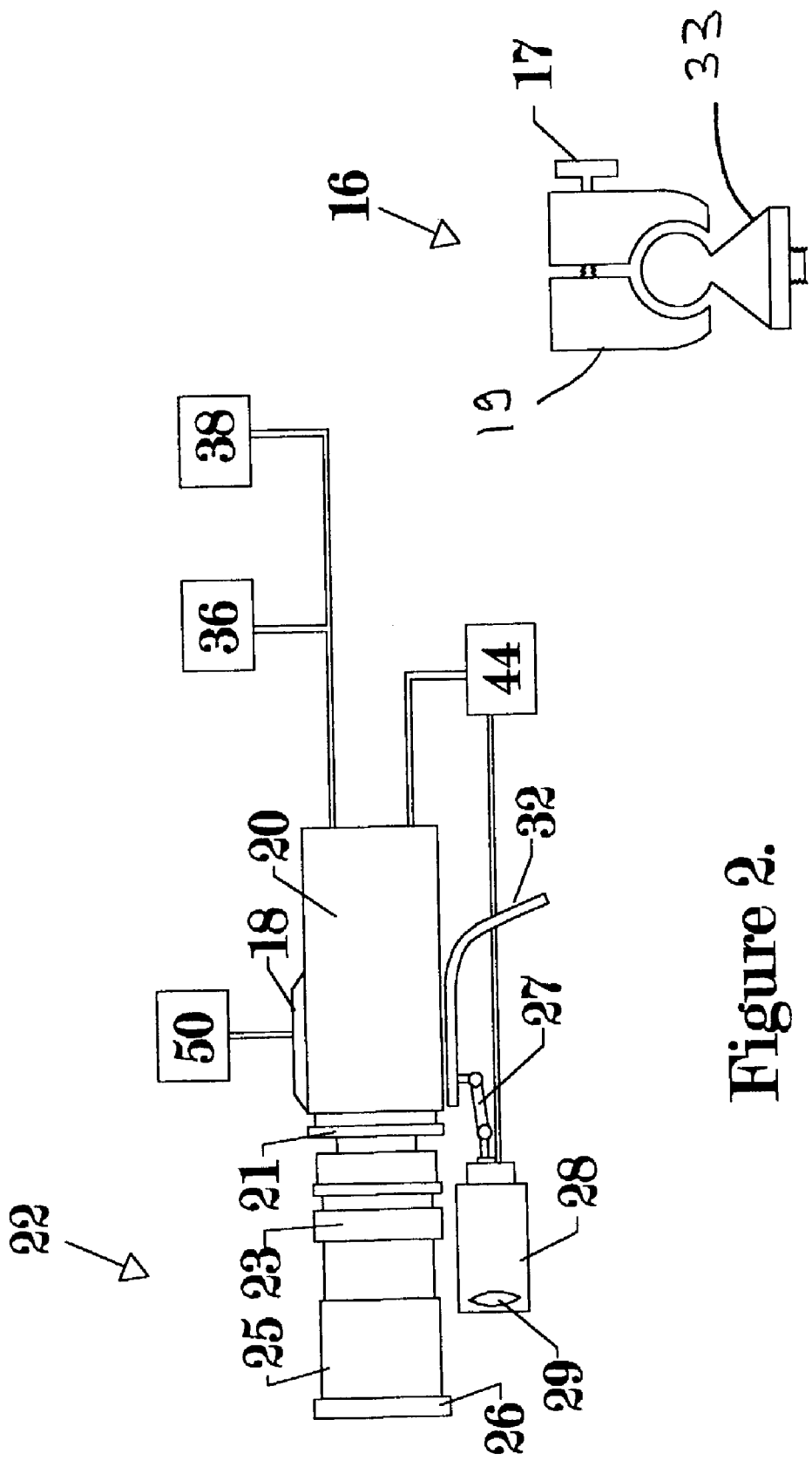

METHOD OF PERFORMING DENTAL WORK AND APPARATUS PROVIDING VISION ENHANCEMENT DENTISTRY

CROSS-REFERENCES TO RELATED APPLICATIONS

This is a continuation-in-part application of Ser. No. 09/451,354 filed on Dec. 13, 1999 now abandoned.

BACKGROUND OF THE INVENTION

1. Field of the Invention

The present invention relates generally to performing dental work and more specifically to a method of performing dental work and apparatus providing vision enhancement dentistry, which visually reproduces and enlarges an operative field.

2. Discussion of the Prior Art

Dentists routinely perform precision detailed restorations in a poorly lit oral cavity. New tooth colored restoratives have placed additional demands on the visual acuity of the practitioner. Age affects the ability of the eye to focus at closer distances and the lens of the eye loses flexibility with age. The lens is unable to accommodate and produce clear images of closer objects. A person reads small print by moving the print further from the eyes until the print becomes clear. This method of focusing makes objects smaller and more difficult to see. Many practitioners will experience the above sight problems, which creates a need to enhance their vision capabilities.

Corrective lenses are used to adjust the visual focal length and improve visual acuity. Without additional magnification, there is a tendency for practitioners to bend over and get closer to an object to increase its size, which leads to poor posture and job stress. Magnification is necessary to perform precision dental procedures.

An optical magnifying lens that attaches to glasses are called magnifying loupes. Loupes provide the wearer with object magnification in a range of 2×-3.25× actual size, providing vision enhancement to the wearer. Some clinical procedures require magnification in the range of 10×, which exceeds the capabilities of loupes. An additional disadvantage of loupes is that they are heavy and uncomfortable to wear, and some clinicians object to wearing loupes for cosmetic reasons.

Operating microscopes provide vision enhancement to operators performing clinical procedures. The operator must look through a microscope eyepiece to view an operative field. The operator must position themselves and their patients in awkward positions to view certain operative fields, a significant disadvantage of operating microscopes. The maximum magnifying capabilities of most operating microscopes exceed the practical requirements of clinical dentistry. Video cameras can be attached to operating microscopes to display magnified images on a video display. The disadvantages of combining video cameras, and operating microscopes include cost, size and weight considerations when adapting an operating microscope to a treatment room.

Video magnification is routinely used in dentistry. U.S. Pat. No. 5,251,025 to Saratoga discloses an electronic video dental camera. U.S. Pat. No. 5,115,307 to Cooper discloses an electronic video dental camera. Video dental cameras, intra-oral cameras, are a part of the general class of endoscopic viewing systems.

Intra-oral cameras are hand-held for viewing an object. The magnification and image quality is adequate for clinical diagnosis and patient communication. However, while holding the intra-oral camera it is difficult for the practitioner to perform clinical tasks with the other hand; a significant disadvantage of using intra-oral cameras. An assistant can not hold the intra-oral camera in a steady consistent position. As the camera orientation is changed it changes the frame of reference of the operator. Without a consistent frame of reference a dental practitioner does not know what direction to move their instruments during clinical procedures, therefore a practitioner cannot do dental work while using an intra-oral camera at the same time.

U.S. Pat. No. 5,803,905 to Allred discloses a surgical camera and light assembly allowing adjustable focus and zoom capability. The camera and light are directed in the same axis and joined together. The surgical camera does not allow adjustment of the focal length of the light beam. The surgical camera does not include the capability of producing a mirror image of an operative field. The surgical camera does not provide a method performing clinical procedures without directly viewing an operative field.

U.S. Pat. No. 6,414,708 to Carmeli et al. discloses a video system for three dimensional imaging and photogrammetry. Dentists can perform dental work while viewing the Carmeli video images. Carmeli's camera provides standard 2D video images and composite 3D video images. However, to function as an understandable frame of reference, the movement of dental instruments from left to right in the mouth, must correspond to movements from left to right across a video screen. Applicant's invention requires a video mirror image to function as a frame of reference for performing dental procedures.

An explanation of the importance of a mirror image and it's relationship to frame of reference is provided in U.S. Pat. No. 6,081,611 to Linford in column 7, line 57 through column 8, line 9. Linford teaches the use of a camera with a mirror image so that a patient will see himself as if looking in a mirror. The reason for this is that when the patient wants to center himself in the monitor he would be inclined to move in the wrong direction if the camera did not have a mirror image. Inventor's dentist and Linford's patient experience a similar viewing perspective and thus experience a similar frame of reference. A dentist moving instruments utilizing the video mirror image as a frame of reference has the same experience as Linford's patient centering himself in the monitor. Conversely, a dentist viewing a standard video image (a non-mirror image) would be inclined to move instruments in the wrong direction.

Inventor was the first to publish an article in the dental literature, utilizing a video camera to perform dental treatment without having to look in the mouth. The article is found in Dentistry Today June 2001, volume 20 Number 6, pages 92-96. A copy of this article will be submitted in the information disclosure statement. However, the article is not prior art, because the parent application was filed, before the article was published. Inventor's camera is a clinically tested, functionally useful system in a typical dental treatment room. It solves stated orthopedic problems of dentists by allowing the dentist to choose their postural position. The dentist is not required to look directly in the mouth. The dentist does not have to bend over to look in the mouth. The camera does the bending for the dentist. The dentist does not have to wear loupes or other devices on his head to enable them to see fine detail. This allows the dentist to position their head without complying with the positional demands of an apparatus, thus eliminating neck and back strain.

Providing magnified video mirror images facilitates clinical visualization of the oral cavity. The dentist can be easily trained to utilize video mirror images as a frame of reference. The typical dentist works with a dental mirror daily. The familiarity with mirror images enables the retraining of dentists for use of inventor's dental camera apparatus. Improved visualization of the oral cavity facilitates precision dental procedures. Back and neck problems caused by excessive bending over patients is a significant occupational health concern of dentists. The need for adequate visualization of the oral cavity is well documented in the dental literature. Inventor's camera system provides a clinically tested solution to both of these problems.

Accordingly, there is a clearly felt need in the art for a method of performing dental work and apparatus providing vision enhancement dentistry, which does not require an operator to hold thereof, enlarges an operative field, and provides a mirror image for proper viewing of the operative field.

SUMMARY OF THE INVENTION

The present invention provides a method of performing dental work and apparatus providing vision enhancement dentistry, which provides an enlarged mirror image of the operative field. The method of performing dental work and apparatus providing vision enhancement dentistry includes a dental camera apparatus. The dental camera apparatus includes a camera assembly, video display and a support assembly. The camera assembly includes a video camera, a camera lens and a light assembly. The camera assembly provides viewing of an operative field on a video display, and enables dental work to be performed without directly viewing a patient's mouth, which is a significant improvement over the prior art. The camera assembly mounts in most treatment rooms, and is easily positioned for viewing of a patient's mouth.

The camera lens assembly includes an adjustable focus, adjustable zoom capability and an adjustable lens opening for magnifying objects. The light assembly includes adjustable positioning and adjustable focus of its light beam for lighting the operative field. The camera assembly provides a magnification of operative fields providing vision enhancement for the viewer. The camera assembly provides viewing of an operative field on a video display, and enables dental work to be performed without directly viewing a patient's mouth.

OBJECTS AND ADVANTAGES OF THE INVENTION

Accordingly, several objects and advantages of my invention are a method of performing dental work without directly viewing an operative field, and an apparatus further providing a means of vision enhancement of the dentist operator. The camera assembly magnifies and provides mirror images to a video display. The camera assembly provides detail that the naked eye can not see. This provides the dentist with a better view of an operative field, improving diagnosis and treatment. Images can be used for clinical demonstration, patient education, or recorded for documentation, and lecturing. The camera assembly includes a macro lens providing adjustable focus and zoom capability. This allows the operator to select the desired magnification and field of vision for a particular procedure. The macro lens provides image clarity over a full range of magnifications, from ultra close up to portrait size.

The camera assembly can be pole mounted, wall mounted, or ceiling mounted to fit conveniently in most treatment rooms. The size and weight of the camera assembly makes it compatible with most existing dental equipment configurations. The mounting assembly provides means of easily directing the video camera from a stable position. The camera assembly has a range of motion that provides viewing of most operative fields. Once the video camera is positioned and adjusted, the operator's hands are free for other instrumentation; this is a significant improvement over prior art. Disposable sleeves are preferably used to protect the lens and camera handle from contamination. The camera assembly includes a lighting device, which provides adjustable positioning and adjustable focus of a high intensity light on an operative field. This allows the operator to adjust the lighting to meet the specific needs of a particular clinical procedure.

The lighting device is used in conjunction with other treatment room lighting. The combination of different light sources provides a synergistic effect, improving the lighting of the operative field. Better lighting provides better visualization and better image reproduction. The camera assembly provides magnified viewing of the operative field on the video display. The camera assembly can be directed from different points of view, providing the operator with different frames of reference. For example, a dentist directly views the right side of a tooth with their eyes, while a live video displays an image of the left side of the tooth. This clinical procedure was traditionally accomplished with the aid of a hand-held mirror.

A magnified video image frees the hands of the operator, and is easier to see. The camera assembly provides a method of performing dental work while viewing the video display. This is a significant departure from and improvement over the traditional method of directly viewing a patient's mouth with a naked eye. This allows dentists to adjust their posture to a comfortable position during clinical procedures. Viewing the video display is less stressful than bending over in an attempt see small objects. Vision enhancement provided by the camera assembly allows the operator to see details the naked eye can not see. Vision enhancement allows the operator to perform precision dental work.

The camera assembly provides a method of displaying mirror images of objects. This is a significant improvement over prior art. This allows the clinician to view images on the video display from a consistent and understandable frame of reference. As a dentist moves instruments across an operative field from left to right, instruments will also move across the video display from left to right. Thus there is a proper correspondence between the clinician's physical sense and what the clinician sees on the video display. This allows the dentist to perform dental work without directly viewing an operative field.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are therefore, not to be considered limiting of its scope, the invention will be described with additional specificity and detail through use of accompanying drawings in which:

FIG. 1 is a side view of a dental camera apparatus in accordance with the present invention;

FIG. 2 is a side view of a camera assembly and accessory components in accordance with the present invention;

FIG. 3 is a cross sectional view of the gooseneck member and internal flexible rod of a dental camera apparatus in accordance with the present invention;

FIG. 4 is a perspective view of ball joint and adjustment knob of a dental camera apparatus in accordance with the present invention;

DETAILED DESCRIPTION OF THE PREFERRED EMBODIMENTS

Figure 5:
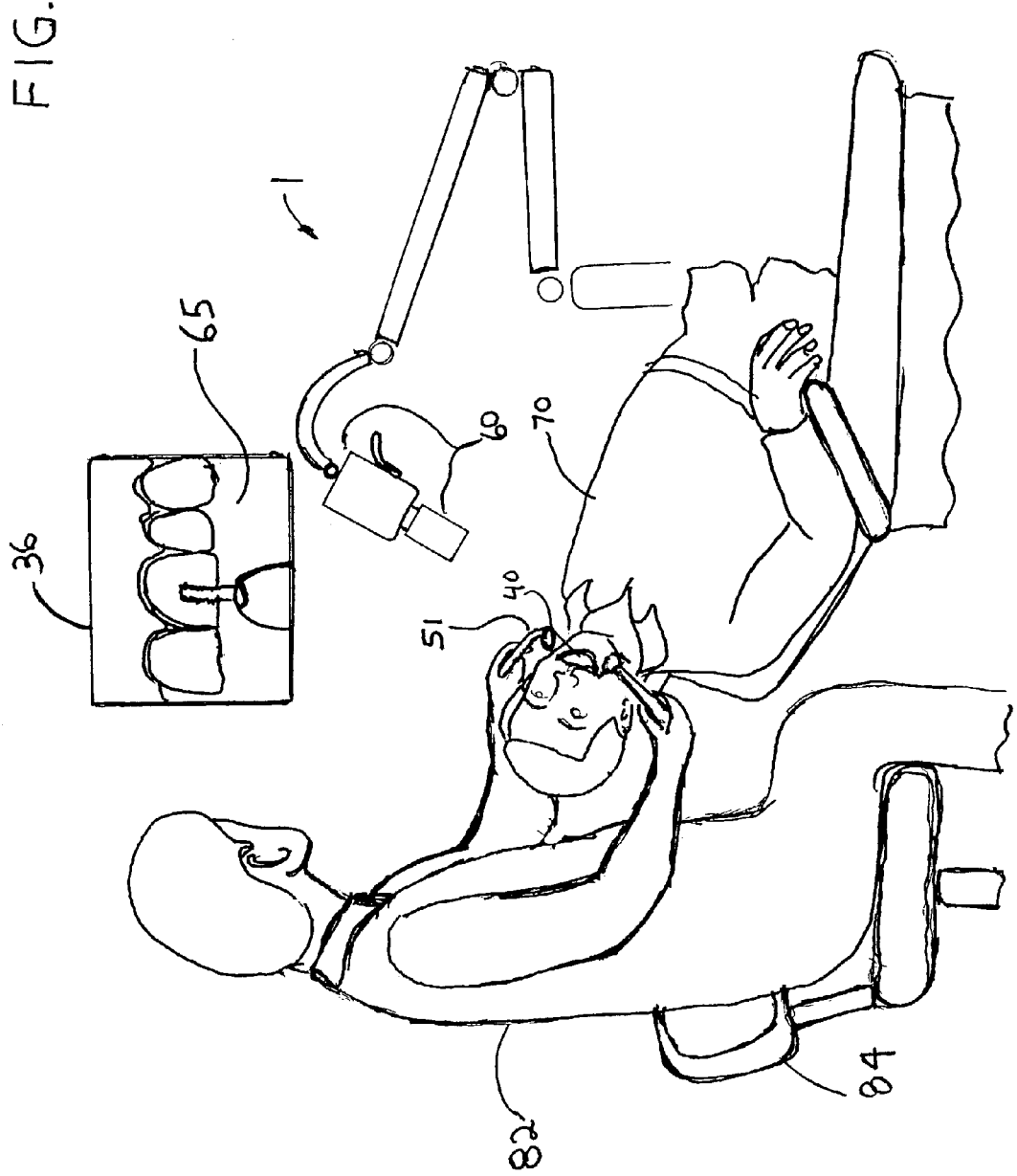
FIG. 5 is a perspective view of a dentist performing dental work without looking directly looking into a mouth of a patient mouth in accordance with the present invention.

It will be readily understood that the components of the present invention, as generally described and illustrated in the FIGS. 1-4, could be arranged and designed in a wide variety of different configurations. Thus, the following more detailed description of the embodiments of the system and methods of the present invention, as represented in FIGS. 1-4 are not intended to limit the scope of the invention, as claimed, but are merely representative of the preferred embodiments of the invention.

The preferred embodiments of the invention will be best understood by reference to the drawings, wherein like parts are designated by like numerals throughout. The preferred embodiment of the dental camera apparatus 1 is designated generally as illustrated FIGS. 1 and 2. The dental camera apparatus includes a support assembly 50. The support assembly 50 includes a support structure 2, a clamp 4, a first articulating extension arm 6, a second articulating extension arm 8, a gooseneck member 12, an internal flexible rod 13, a ball joint 16 and a mounting plate 18.

The support structure 2, could be mounted to a floor, wall, ceiling, or a clinical patient chair or table. The clamp 4 is affixed to the support structure 2. The clamp 4 is pivotally attached to the first articulating extension arm 6, which is pivotally attached to the second articulating extension arm 8. One end of the gooseneck member is attached to one end of the second articulating extension arm 8 with a swivel joint 10.

The internal flexible rod 13 decreases the flexibility of the gooseneck member 12. The flexible rod 13, is sized to support the weight of a camera assembly 60. With reference to FIGS. 1 and 2, the camera assembly 60 includes a video camera 20, an optical lens 22, a lens mounting assembly 21, a lighting device 28, and a handle 32. The flexible rod 13 provides a means of adjusting the weight supporting capability of the gooseneck member 12, which is an improvement over the prior art. A ball joint 16 is attached to the other end of the gooseneck 12. The ball joint 16 preferably includes a clamp member 19 and a ball member 33. The clamp member 19 includes an adjustment knob 17. The adjustment knob 17 may be tightened to prevent rotation of the ball joint 16, or loosened to allow rotation of the ball joint 16, with varying applications of force. A mounting plate 18 is attached to the video camera 20. The ball joint 16 is affixed to a mounting plate 18. The video camera 20 is electrical connected to a power supply 44, a video display 36 and preferably a video recording device 38. The video recording device 38 is preferably a VCR, but other recording devices may also be used.

The video camera 20, converts optical images received by the optical lens 22 into electrical signals. The dental camera apparatus 1 further includes a video display 36, which receives the electrical signals from the video camera 20. The video camera 20 is electrically connected to the video display 36 by a wire or wireless connection.

It is to be appreciated that the support assembly 50, combines the functional capabilities of the articulating extension arms, the swivel joint 10, the gooseneck member 12, the internal flexible rod 13, and the ball joint 16. The support assembly 50 is highly suitable for the present application. The combined range of motion of the components, make the invention adaptable in a wide range of clinical applications. The support assembly 50 will retain its set position and enable the video camera 20, to be positioned for extreme close-ups without concern of movement of the video camera 20.

The support assembly 50 provides a functional engagement with the camera assembly 60. The support assembly 50 allows the camera assembly 60 to be positioned and stabilized. The support assembly 50 can be adapted to function with most existing treatment room configurations.

A lens mounting assembly 21 is affixed to the video camera 20. The optical lens 22 is attachable to the lens mounting assembly 21. The optical lens 22 provides visual images of an operative field 40. The operative field 40 could represent a wide range of medical and dental clinical operative fields, including a human mouth. The optical lens 22 includes a zoom focus adjustment ring 23, a variable focus an adjustment ring 25 and means for adjusting the focus and zoom capability. The optical lens 22 is preferably a Computar R TV macro zoom lens model number MLH-10X. However, other optical lens may also be used.

The optical lens 22 provides ultra close-up images of the operative field 40. The magnification of an object is dependent upon the magnifying power of the optical lens 22, screen size of the video display 36 and the position of the camera assembly 60 relative to an object. The optical lens 22 provides a choice of magnifications from actual size to fifty times actual size. As the magnification increases, the operator's field of view decreases. Dentists will normally choose a field of view that is appropriate for a specific procedure. In use, the operator positions the camera assembly 60 adjacent the operative field 40 and then rotates the zoom focus adjustment ring 23 to select the desired field of view. The focus adjustment ring 25 is rotated to obtain a sharp focus. Dentists most commonly utilize magnifications between 3 and 20 times actual size, which is within the capabilities of the optical lens 22.

The goal of the dental camera apparatus 1 is to enhance the vision of the operator beyond the capability of the naked eye. Operators utilize the magnifying and focusing capability of the dental camera assembly 60 to enhance their vision. The dental camera apparatus 1 is an alternative to operating microscopes and optical magnifying loupes. The operator of the dental camera apparatus 1 can view magnified objects indirectly on the video display 36 without having to look directly through a lens. This is a significant improvement over prior art. Preferably, a lens filter 26 is affixed to the optical lens 22. The lens filter 26 protects the lens 22 from clinical contamination or damage from scratching.

A handle 32 preferably extends from the video camera 20. The handle 32 allows repositioning of the camera assembly 60. The handle 32 could be designed in a multiplicity of forms. Alternative embodiments of the invention could have the handle 32, affixed to different components of the camera assembly 60 or the support assembly 50.

A lighting device 28 is preferably attached to the handle 32 with an intermediate light directing member 27. The lighting device 28 illuminates the operative field 40. The lighting device 28 includes a lens 29 providing means of focusing a high intensity light on the desired area of an operative field 40. Moving the lens 29 relative to the high intensity light, focuses the lighting device 28. The lighting device 28 preferably utilizes a DC power supply 44, and a 10-watt bulb. Alternative embodiments could include a fiber optic lighting device.

Different clinical procedures require different lighting conditions. The lighting device 28, the light directing means 27 and the light focusing lens 29, enable direction and focusing of a high intensity light source to effectively light an operative field 40. Proper lighting is essential to providing sharp, clear, well focused video images. The handle 32 and lens 22 can be wrapped with disposable plastic sheaths to meet the disinfecting requirements for medical equipment in a clinical setting. The lens filter 26 can be removed and sterilized.

The video camera 20 also includes the capability of producing color video images. The video camera 20 is also capable of electronically inverting visual images. The video camera 20 is preferably a Panasonic R color CCTV camera model WV-CP650, which was chosen for it's high resolution capability and it's capability to electronically invert visual images. The video camera 20 is equipped with a CCD sensor having 370,000 pixels, which yields 480 lines of horizontal resolution. The electronics of the video camera 20 provide for a so-called white balance circuit which constantly corrects the white balance level, thereby optimizing color rendition at all times, regardless of varying ambient light conditions.

The electronics of video camera 20 also includes a noise reduction circuit with a signal-to-noise ratio that provides high quality color and signal at all light levels. The camera also includes a $\frac{1}{1000}$ of a second electronic high speed shutter; selective from $\frac{1}{60}$ normal to $\frac{1}{1000}$ second in which the higher shutter speed will track very rapid medical movements, thus producing clear still frames and slow motion upon VCR playback. The camera is also furnished with the capability of automatic switching of internal/external synchronization, and is genlockable providing for easy adaptation to ready existing systems and/or to provide itself with internal synchronization. However, other video cameras besides the Panasonic camera may also be used.

The camera assembly 60 provides the display of the mirror image of objects, unlike that of the prior art. The mirror image capability allows a clinician to view images on a video display 36, from a consistent and understandable frame of reference. As a dentist moves instruments across an operative field 40, from left to right, the instruments also move across the video display 36, from left to right. The dental camera apparatus 1 provides a proper correspondence between the clinician's physical sense and what the clinician sees on a video display 36. This allows dentists to perform dental work without directly viewing a patient's mouth.

The ability of the Panasonic R video camera to provide mirror images is accomplished by selecting the command "up side down" from the camera set up menu. The "up side down" image can be converted to a mirror image by turning the Panasonic R camera upside down. The mounting plate 18 is normally at a bottom of the Panasonic R video camera but the video camera 20 is rotated 180 degrees to provide a mirror image of an object. Mirror images provide an understandable frame of reference for a viewer. The frame of reference enables an operator to perform clinical procedures without directly viewing the operative field 40.

Figure 6:
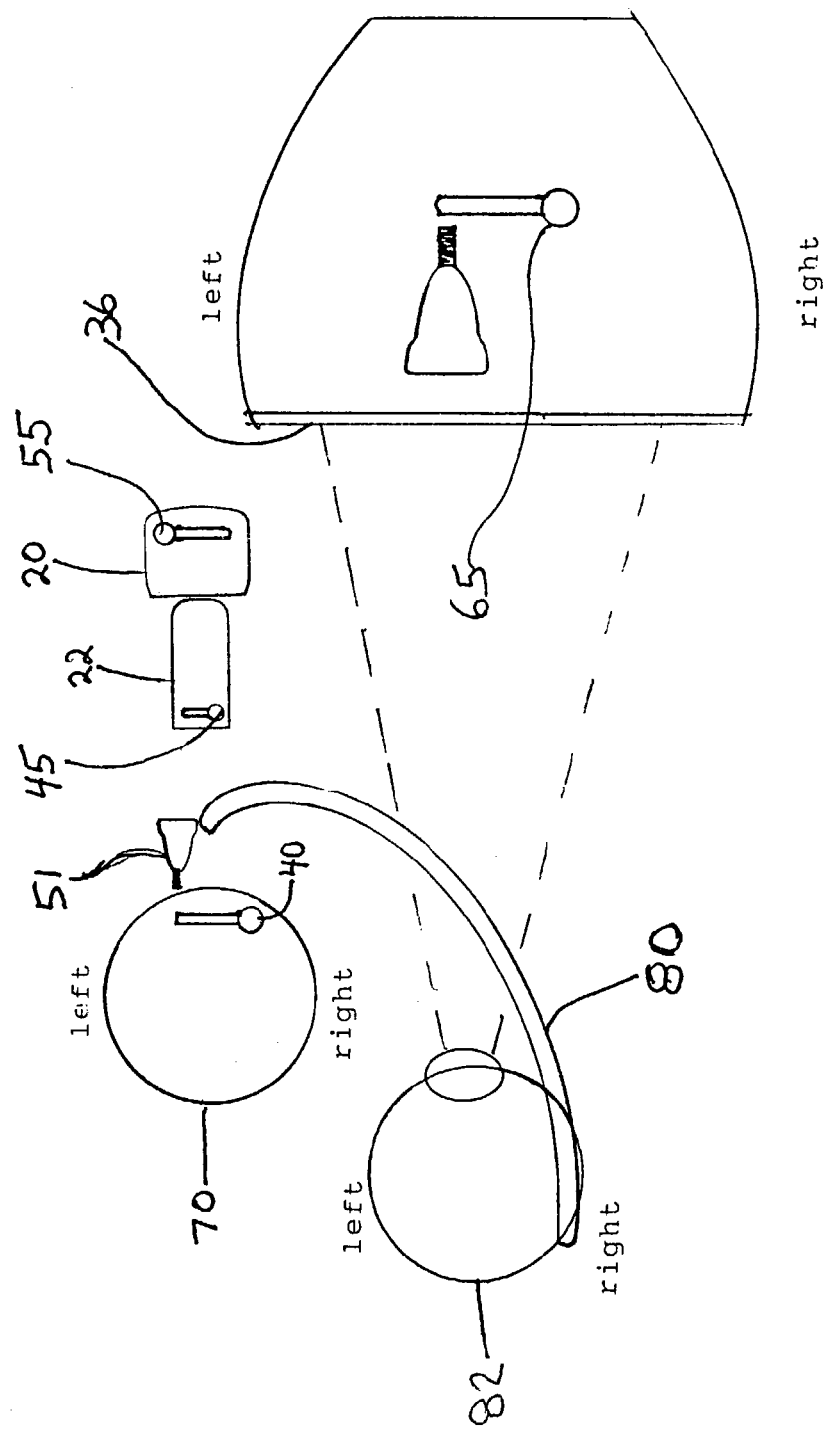
FIG. 6 is a top schematic view illustrating a dental camera apparatus being used to perform dental in accordance with the present invention.

FIG. 5 shows a perspective view of a dentist 82 performing dental work on a patient 70 without looking directly into their mouth. The diagram illustrates typical positions of a dentist 82 and patient 70 during dental treatment. FIG. 6 is a top schematic view illustrating the dentist 82 performing dental work on a patient 70 without looking directly into their mouth. The dentist 82 views a magnified video mirror image 65 of an operative field 40. The video mirror image 65 functions as an understandable frame of reference enabling the dentist 82 to perform dental work. The dental camera apparatus 1 is a significant improvement over prior art.

Patients normally recline for dental treatment. The dentist 82 typically sits along side of the patient 82, or behind the patient's reclined head. The dentist 80 does not have to bend over to view the operative field 40. The camera assembly 60, can be positioned at any desired viewing angle to provide the desired view of the operative field 40. A dental assistant or dentist repositions the camera assembly 60 as necessary. The camera assembly 60 remains in a stable position and the dentist's hands are free for manipulating dental instruments 51. The camera assembly 60, does not interfere with the dental instruments 51, or staff positioning.

The video display 36 is normally located at eye level. The video display 36 is preferably located at a side of a chair 84 and not at the foot of the chair 84. The dental camera apparatus 1 allows the dentist to maintain a comfortable working position while viewing the video display 36, thus preventing back and neck strain. The camera assembly 60, provides a mirror image of the operative field 40. The video display 36 shows a magnified video mirror image 65 of the operative field 40. The magnified video mirror image 65, enables the dentist 80 to view details the unaided eye can not see. The dental camera apparatus 1 facilitates precision dental procedures.

The magnified video mirror image 65, provides an understandable frame of reference for the dentist, which enables the dentist to perform dental work without looking directly in a patient's mouth. The typical dentist uses a dental mirror daily. The video mirror image 65 is functionally equivalent to an image provided by a dental mirror. Familiarity with a mirror image enables dentists to be easily retrained for the dental camera apparatus 1. The dentist 82 can directly view an operative field 40, utilize a standard dental mirror to view an operative field 40, or view a magnified video mirror image 65 of an operative field 40. Typically, the eyes shift between all of these views, as clinical demands change. The ability to choose a viewing perspective, while maintaining an ergonomic correct body position is a significant improvement over prior art.

With reference to FIG. 6, the optical lens 22 is positioned to provide the desired view of the operative field 40. The optical lens 22 provides a visual image 45 of the operative field 40. The video camera 20 electronically converts the visual image 45 into a video mirror image 55. The video display 36 shows the magnified video mirror image 65 of the operative field 40. The dentist 82 views the magnified video mirror image 65 and utilizes the magnified video mirror image 65, as an understandable frame of reference 40. Dental instruments 51, can be moved relative to an operative field 40, while viewing the magnified video mirror image 65. As the dentist 82 moves instruments across an operative field 40, from left to right, the dental instruments 51 also move across the video display 36, from left to right. Thus there is proper correspondence between the clinician's physical sense and what the clinician sees on the video display 36. The dental camera apparatus 1 enables a dentist 82, to perform dental work 80, while viewing the magnified video mirror image 65. The dental camera apparatus 1 is a significant improvement over prior art.

Accordingly, while there has been shown and described the preferred embodiment of the present invention, it will be understood that the invention may be embodied otherwise than is herein illustrated and described and that, within said embodiment, certain changes may be made in the detail and construction, in the form and arrangement of the parts without departing from the underlying idea or principles of this invention within the scope of the claims appended herewith.

I claim:

1. A method of providing an enhanced image of an operative field, comprising the steps of:

providing a video camera that is positioned to provide a mirror image of an operative field, said mirror image providing an understandable frame of reference of the operative field, said video camera being located outside a human mouth, said video camera not entering into the human mouth for the process of providing the enhanced image; and providing an adjustable support structure for retaining said video camera in a stationary position outside the human mouth; and displaying the operative field on a video display device, the operative field being an enlarged image of an open patient's mouth for the performance of dental work therein, wherein a user being able to switch between viewing said video display device and directly viewing said operative field to perform movements with an instrument.

2. The method of providing an enhanced image of an operative field of claim 1, further comprising the step of:

providing a lighting device.

3. The method of providing an enhanced image of an operative field of claim 2, further comprising the step of:

making said lighting device independently adjustable relative to said video camera.

4. The method of providing an enhanced image of an operative field of claim 1, further comprising the step of:

providing said adjustable support structure with a first extension arm, a second extension arm and a gooseneck member, one end of said first extension arm being pivotally attached to said support structure, the other end of said first extension arm being pivotally attached to one end of said second extension arm, the other end of said second extension arm being attached to one end of said gooseneck member, the other end of said gooseneck member being attached to said video camera.

5. The method of providing an enhanced image of an operative field of claim 4, further comprising the step of:

providing said gooseneck member with an internal flexible rod sized to support the weight of said video camera.

6. The method of providing an enhanced image of an operative field of claim 1, further comprising the step of:

providing said video camera with color video capability.

7. The method of providing an enhanced image of an operative field of claim 1, further comprising the step of:

enlarging the operative field for viewing on said video display device.

8. The method of providing an enhanced image of an operative field of claim 1, further comprising the step of:

providing said optical lens with variable focus and zoom capability.

9. A method of performing dental work by viewing a video display device, comprising the steps of:

providing a video camera that is positioned to provide a mirror image of the operative field, said mirror image providing an understandable frame of reference of the operative field, said video camera being located outside a human mouth, said video camera not entering into the human mouth for the process of providing the enhanced image;

providing an adjustable support structure for retaining said video camera in a stationary position outside the human mouth; and displaying the operative field on a video display device, the operative field being an enlarged image of an open patient's mouth for the performance of dental work therein.

10. The method of performing dental work by viewing a video display device of claim 9, further comprising the step of:

providing a lighting device.

11. The method of performing dental work by viewing a video display device of claim 10, further comprising the step of:

making said lightening device independently adjustable relative to said video camera.

12. The method of performing dental work by viewing a video display device of claim 9, further comprising the step of:

providing said adjustable support structure with a first extension arm, a second extension arm and a gooseneck member, one end of said first extension arm being pivotally attached to said support structure, the other end of said first extension arm being pivotally attached to one end of said second extension arm, the other end of said second extension arm being attached to one end of said gooseneck member, the other end of said gooseneck member being attached to said video camera.

13. The method of performing dental work by viewing a video display device of claim 12, further comprising the step of:

providing said gooseneck member with an internal flexible rod sized to support the weight of said video camera.

14. The method of performing dental work by viewing a video display device of claim 9, further comprising the step of:

providing said video camera with color video capability.

15. The method of performing dental work by viewing a video display device of claim 9, further comprising the step of:

enlarging the operative field for viewing on said video display device.

16. The method of performing dental work by viewing a video display device of claim 9, further comprising the step of:

providing said optical lens with variable focus and zoom capability.

17. The method of performing dental work by viewing a video display device of claim 9, further comprising the step of:

positioning said video camera and said video display device in front of a patient.

* * * * *